United States Patent
Dixon et al.

(10) Patent No.: US 9,383,251 B2
(45) Date of Patent: *Jul. 5, 2016

(54) HOSPITAL BED HAVING WEIGH SCALE SYSTEM

(71) Applicant: Hill-Rom Services, Inc., Batesville, IN (US)

(72) Inventors: Steven A. Dixon, Cincinnati, OH (US); Jeffrey R. Welling, Goose Creek, SC (US); James R. Stolpmann, Bakersville, NC (US); Andrew F. Skinner, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/475,622

(22) Filed: Sep. 3, 2014

(65) Prior Publication Data

US 2015/0008049 A1 Jan. 8, 2015

Related U.S. Application Data

(60) Continuation of application No. 13/281,988, filed on Oct. 26, 2011, now Pat. No. 8,827,931, which is a division of application No. 12/367,877, filed on Feb. 9, 2009, now Pat. No. 8,048,005, which is a continuation (Continued)

(51) Int. Cl.
*G01G 19/52* (2006.01)
*A61B 5/11* (2006.01)

(Continued)

(52) U.S. Cl.
CPC .............. *G01G 19/52* (2013.01); *A61B 5/1115* (2013.01); *A61G 7/00* (2013.01); *A61G 7/002* (2013.01);

(Continued)

(58) Field of Classification Search
CPC ... A61B 5/1115; A61G 7/005; A61G 7/0008; A61G 7/012; A61G 7/015; A61G 7/018; A61G 7/05; A61G 7/0504; A61G 7/0507; A61G 7/05769; A61G 2007/0509; A61G 2007/051; A61G 2007/0514; A61G 2007/0527; A61G 2203/32; A61G 2203/34; A61G 2203/74; A61G 2203/44; A61G 2203/42; A61G 7/0506; B60B 33/0002; B60B 33/0021; B60B 33/0042; B60B 33/0049; B60B 33/0057; B60B 33/0068; B60B 33/0073; B60B 33/021; G01G 5/006; G01G 19/445; G01G 19/52; G01G 23/36; G08B 3/10

USPC ........ 600/587, 595; 177/1, 45, 126–127, 144; 5/710, 713–715, 914; 340/573.1, 340/666–667

See application file for complete search history.

(56) References Cited

U.S. PATENT DOCUMENTS 1,078,077 A 11/1913 Arnold
2,527,111 A 10/1950 Widrich et al.

(Continued)

FOREIGN PATENT DOCUMENTS

DE 3313843 A1 10/1984
DE 3716917 A1 12/1988

(Continued)

OTHER PUBLICATIONS

Prior Art emme3 Bed Brochure, purported by Defendants to have been published circa Mar. 1996 ("emme3 Bed Brochure Italian").

(Continued)

*Primary Examiner* — Rene Towa
(74) *Attorney, Agent, or Firm* — Barnes & Thornburg LLP

(57) ABSTRACT

A hospital bed includes a force sensor or scale apparatus configured to detect the weight of a patient.

22 Claims, 13 Drawing Sheets

Related U.S. Application Data of application No. 10/508,359, filed as application No. PCT/US03/08189 on Mar. 18, 2003, now Pat. No. 7,500,280.

(60) Provisional application No. 60/408,698, filed on Sep. 6, 2002, provisional application No. 60/436,289, filed on Dec. 23, 2002, provisional application No. 60/365,295, filed on Mar. 18, 2002.

(51) Int. Cl.

| | |
|---|---|
| *A61G 7/00* | (2006.01) |
| *A61G 7/002* | (2006.01) |
| *A61G 7/005* | (2006.01) |
| *A61G 7/008* | (2006.01) |
| *A61G 7/012* | (2006.01) |
| *A61G 7/015* | (2006.01) |
| *A61G 7/018* | (2006.01) |
| *A61G 7/05* | (2006.01) |
| *A61G 7/057* | (2006.01) |
| *B60B 33/00* | (2006.01) |
| *B60B 33/02* | (2006.01) |
| *G01G 5/00* | (2006.01) |
| *G01G 19/44* | (2006.01) |
| *G01G 23/36* | (2006.01) |
| *G08B 3/10* | (2006.01) |
| *G08B 5/36* | (2006.01) |

(52) U.S. Cl.
CPC .............. *A61G 7/005* (2013.01); *A61G 7/008* (2013.01); *A61G 7/012* (2013.01); *A61G 7/015* (2013.01); *A61G 7/018* (2013.01); *A61G 7/05* (2013.01); *A61G 7/0504* (2013.01); *A61G 7/0507* (2013.01); *A61G 7/05715* (2013.01); *A61G 7/05769* (2013.01); *B60B 33/0002* (2013.01); *B60B 33/0021* (2013.01); *B60B 33/0042* (2013.01); *B60B 33/0049* (2013.01); *B60B 33/0057* (2013.01); *B60B 33/0068* (2013.01); *B60B 33/0073* (2013.01); *B60B 33/021* (2013.01); *G01G 5/006* (2013.01); *G01G 19/445* (2013.01); *G01G 23/36* (2013.01); *G08B 3/10* (2013.01); *G08B 5/36* (2013.01); *A61G 7/0506* (2013.01); *A61G 2007/051* (2013.01); *A61G 2007/0509* (2013.01); *A61G 2007/0514* (2013.01); *A61G 2007/0527* (2013.01); *A61G 2203/32* (2013.01); *A61G 2203/34* (2013.01); *A61G 2203/42* (2013.01); *A61G 2203/44* (2013.01); *A61G 2203/74* (2013.01)

(56) References Cited

U.S. PATENT DOCUMENTS

| | | | | |
|---|---|---|---|---|
| 3,605,668 | A | * | 9/1971 | Morgan .................. 114/293 |
| 4,205,379 | A | * | 5/1980 | Fox et al. ................ 701/116 |
| 4,686,722 | A | | 8/1987 | Swart |
| 4,869,266 | A | * | 9/1989 | Taylor et al. ................ 600/587 |
| 4,921,295 | A | | 5/1990 | Stollenwerk |
| 5,044,029 | A | * | 9/1991 | Vrzalik ..................... 5/713 |
| 5,276,432 | A | | 1/1994 | Travis |
| 5,393,935 | A | | 2/1995 | Hasty et al. |
| 5,611,096 | A | | 3/1997 | Bartlett et al. |
| 5,646,376 | A | | 7/1997 | Kroll et al. |
| 5,691,932 | A | | 11/1997 | Reiner et al. |
| 5,715,548 | A | | 2/1998 | Weismiller et al. |
| 5,873,137 | A | | 2/1999 | Yavets-Chen |
| 6,199,508 | B1 | | 3/2001 | Miale et al. |
| 6,244,121 | B1 | | 6/2001 | Hunter |
| 6,282,736 | B1 | | 9/2001 | Hand et al. |
| 6,336,235 | B1 | | 1/2002 | Ruehl |
| 6,351,861 | B1 | | 3/2002 | Shows et al. |
| 6,353,950 | B1 | | 3/2002 | Bartlett et al. |
| 6,469,263 | B1 | | 10/2002 | Johnson |
| 6,646,556 | B1 | | 11/2003 | Smith et al. |
| 6,912,746 | B2 | | 7/2005 | Grove |
| 7,500,280 | B2 | | 3/2009 | Dixon et al. |
| 8,048,005 | B2 | | 11/2011 | Dixon et al. |
| 8,827,931 | B2 | | 9/2014 | Dixon et al. |
| 2002/0021278 | A1 | * | 2/2002 | Hinckley et al. .............. 345/156 |
| 2002/0196148 | A1 | | 12/2002 | Nunome |

FOREIGN PATENT DOCUMENTS

| | | |
|---|---|---|
| EP | 1415630 | 5/2004 |
| GB | 2344283 | 6/2000 |
| JP | 2-156950 | 6/1990 |
| JP | 11299837 | 11/1999 |
| WO | WO 97/20534 | 6/1997 |

OTHER PUBLICATIONS

Prior Art emme3 Bed Brochure, purported by Defendants to have been published circa May 1997 ("emme3 Bed Brochure English").

Prior Art emme3 Instructions for Use, purported by Defendants to have been published circa Mar. 1998 (emme3 Instructions).

Complaint (filed Jun. 17, 2010 by Plaintiffs, Hill-Rom, Inc. Hill-Rom Services and Hill-Rom Company).

Answer and Counterclaims of Defendants Huntleigh Healthcare LLC and Huntleigh Healthcare, Inc. to the Complaint of Hill-Rom, Inc., Hil-Rom Services, Inc., and Hill-Rom Company, Inc. (filed Aug. 5, 2010 by Defendants Huntleigh Healthcare LLC and Huntleigh Healthcare, Inc.).

Reply to Counterclaims (filed Aug. 16, 2010 by Plaintiffs, Hill-Rom, Inc. Hill-Rom Services and Hill-Rom Company).

Plaintiff Hill-Rom's First Set of Interrogatories to Defendant (filed Sep. 17, 2010 by Plaintiffs, Hill-Rom, Inc. Hill-Rom Services and Hill-Rom Company).

Plaintiff Hill-Rom's First Request for the Production of Documents and Things to Defendant Huntleigh (filed Sep. 17, 2010 by Plaintiffs, Hill-Rom, Inc. Hill-Rom Services and Hill-Rom Company).

Huntleigh Healthcare LLC's First Request to Hill-Rom Services, Inc. for Production of Documents and Things (filed Sep. 22, 2010 by Defendants Huntleigh Healthcare LLC and Huntleigh Healthcare, Inc.).

Huntleigh Healthcare LLC's First Request to Hill-Rom Company, Inc. for Production of Documents and Things (filed Sep. 22, 2010 by Defendants Huntleigh Healthcare LLC and Huntleigh Healthcare, Inc.).

Huntleigh Healthcare LLC's First Request to Hill-Rom, Inc. for Production of Documents and Things (filed Sep. 22, 2010 by Defendants Huntleigh Healthcare LLC and Huntleigh Healthcare, Inc.).

Defendant Hunteligh Healthcare LLC's First Set of Interrogatories (Nos. 1-11) to Plaintiff Hill-Rom Company, Inc. (filed Sep. 22, 2010 by Defendants Huntleigh Healthcare LLC and Huntleigh Healthcare, Inc.).

Defendant Hungleigh Healthcare LLC's First Set of Interrogatories (Nos. 1-11) to Plaintiff Hill-Rom Services, Inc. (filed Sep. 22, 2010 by Defendants Huntleigh Healthcare LLC and Huntleigh Healthcare, Inc.).

Defendant Huntleigh Healthcare LLC's First Set of Interrogatories (Nos. 1-11) to Plaintiff Hill-Rom, Inc. (filed Sep. 22, 2010 by Defendants Huntleigh Healthcare LLC and Huntleigh Healthcare, Inc.).

Hill-Rom's Initial Disclosures (filed Sep. 30, 2010 by Plaintiffs, Hill-Rom, Inc. Hill-Rom Services and Hill-Rom Company).

Initial Disclosures for Defendants Huntleigh Healthcare LLC, and Huntleigh Healthcare, Inc. (filed Sep. 30, 2010 by Defendants Huntleigh Healthcare LLC and Huntleigh Healthcare, Inc.).

Case Management Plan Order (filed Nov. 5, 2010).

Plaintiffs' Preliminary Infringement Contentions (filed Nov. 5, 2010 by Plaintiffs, Hill-Rom, Inc. Hill-Rom Services and Hill-Rom Company).

(56) References Cited

OTHER PUBLICATIONS

Responses and Objections of Defendants Huntleigh Healthcare LLC and Huntleigh Healthcare Inc. to Plaintiff Hil-Rom's First Set of Interrogatories (1-5) (filed Nov. 18, 2010 by Defendants Huntleigh Healthcare LLC and Huntleigh Healthcare, Inc.).

Responses and Objections of Defendants Huntleigh Healthcare LLC and Huntleigh Healthcare Inc to Plaintiff Hill-Rom's First Request for Documents and Things (filed Nov. 18, 2010 by Defendants Huntleigh Healthcare LLC and Huntleigh Healthcare, Inc.).

Plaintiffs' Hill-Rom, Inc.'s Hill-Rom Services, Inc.'s and Hill-Rom Company, Inc.'s Consolidated Answers and Objections to Defendant Huntleigh Healthcare LLC's First Set of Interrogatories (Nos. 1-11) (filed Nov. 22, 2010 by Plaintiffs, Hill-Rom, Inc. Hill-Rom Services and Hill-Rom Company).

Plaintiffs' Hill-Rom, Inc.'s, Hill-Rom Services, Inc.'s and Hill-Rom Company, Inc.'s Consolidated Responses and Objections to Defendant Hunteligh Healthcare LLC's First Request for Production of Documents and Things (filed Nov. 22, 2010 by Plaintiffs, Hill-Rom, Inc. Hill-Rom Services and Hill-Rom Company).

Defendants' Preliminary Invalidity Contentions (filed Dec. 22, 2010 by Defendants Huntleigh Healthcare LLC and Huntleigh Healthcare, Inc.)—Exhibits A-H.

European search report from related EP 10 17 6912 dated Apr. 4, 2014, 6 pages.

* cited by examiner $f_2' = f_2$
$\cos \theta = f_1/W$
$W = f_1/\cos \theta$

Table 1 — 1078

| Input | | Output | |
|---|---|---|---|
| Head Angle (A) | Seat Force (F') | Weight (W) | Limits (L) |
|  |  |  |  |
|  |  |  |  |
|  |  |  |  |
|  |  |  |  |

FIG. 16

Table 2 — 1080

| Input | | Output | | |
|---|---|---|---|---|
| Weight (W) | Seat Force (F') | P1 | P2 | P3 |
|  |  |  |  |  |
|  |  |  |  |  |
|  |  |  |  |  |
|  |  |  |  |  |

FIG. 17

HOSPITAL BED HAVING WEIGH SCALE SYSTEM

This application is continuation of U.S. application Ser. No. 13/281,988, filed Oct. 26, 2011, now U.S. Pat. No. 8,827, 931, which is a divisional of U.S. application Ser. No. 12/367, 877, filed Feb. 9, 2009, now U.S. Pat. No. 8,048,005, which is a continuation of U.S. application Ser. No. 10/508,359, filed Mar. 25, 2005, now U.S. Pat. No. 7,500,280, which is the U.S. national stage entry under 35 U.S.C. 371 of PCT Application No. PCT/US2003/008189, filed Mar. 18, 2003, which claims the benefit of U.S. Provisional Application No. 60/408,698, filed Sep. 6, 2002, U.S. Provisional Application No. 60/436, 289, filed Dec. 23, 2002, and U.S. Provisional Application No. 60/365,295, filed Mar. 18, 2002, the disclosures of all of which are expressly incorporated by reference herein.

BACKGROUND AND SUMMARY OF THE INVENTION

The present invention relates generally to hospital beds and, more particularly, to a hospital bed having a force or weight sensor.

It is known for beds to have scales which automatically provide a patient's weight to a caregiver. Various types of such scales are known. See, for example, U.S. Pat. Nos. 6,208,250; 5,859,390; 5,173,977; 4,961,470; 4,281,730; 4,953,244; 4,793,428; 5,269,388; and 5,279,010 all of which are incorporated by reference herein. These scales allow caregivers to weigh patients without having them leave the bed. Some beds have built in weigh frames with load cells located beneath the weigh frames.

Many hospital beds permit articulation of their patient support decks for relative positioning or elevation of the head, legs, and feet of a patient to suit various therapeutic needs. Moreover, many hospital beds permit adjustment of their patient support decks from a normal horizontal position to an angled head down or head up position—so called "Trendelenburg" and "reverse Trendelenburg" positions, respectively. Some force sensors, such as load cells of a bed scale, are mounted to a movable frame of a bed instead of a stationary base frame. In such embodiments, when the movable frame is aligned at an angle, the measured weight of the patient is inaccurate because the direction of the weight force is not perpendicular to load cells of the weigh system.

An illustrative embodiment of the present invention provides a system which determines an angle of alignment of the movable frame in at least one direction and corrects the force measured by the force sensor to generate a corrected weight. Therefore, the system provides an accurate weight reading even when the movable frame of the bed is aligned at a non-horizontal angle.

Hospital beds with pressurized air mattresses are also common. Optimizing mattress pressures helps patients feel more comfortable. Additionally, providing optimum mattress pressures reduces interface pressure against the patient and therefore reduces the likelihood of bed sores and other problems associated with being bed ridden for long periods of time. A patient's size and weight are common factors for determining an optimum mattress pressure. Accordingly, some hospital beds have controllers programmed with several weight ranges and respective mattress pressures. In these systems, a caregiver manually inputs the patient's weight or presses a button corresponding to a weight range, and the controller then maintains predetermined pressures in the air mattress based on the weight setting. However, such beds require the caregiver to know the patient's weight and manually input the weight.

A further illustrative embodiment of the present invention provides a control system which automatically adjusts pressure in an inflatable portion of a patient support based on a patients weight detected by a force sensor or other scale apparatus.

According to another illustrative embodiment of the present invention, an apparatus for supporting a patient is provided. The patient has a mass accelerated by gravity to produce a weight force having a vertical direction. The weight force is conceivable as a sum of component forces including a first force vector having a first magnitude, and a second force vector having a second magnitude. The first force vector has a first direction aligned at angle relative to the direction of the weight force, and the second force vector has a second direction perpendicular to the first direction. The apparatus includes a supply configured to receive a control signal and supply a compressible medium in response to the control signal, and a patient support including an inflatable portion coupled to the supply to receive the compressible medium therefrom. The inflatable portion is configured to be pressurized by the compressible medium. The apparatus further includes a pressure sensor coupled to the inflatable portion of the patient support to be exposed to the pressure therein, the pressure sensor being configured to generate a pressure signal in response to the pressure. A force sensor is positioned to detect the first magnitude of the first force vector, the force sensor being configured to generate a force signal in response to the first magnitude. A controller is coupled to the pressure sensor to receive the pressure signal therefrom and is coupled to the force sensor to receive the force signal therefrom. The controller is configured to generate the control signal in response to the pressure signal and the force signal.

According to a further illustrative embodiment of the present invention, a method for supporting a patient on a patient support is provided. The method comprises pressurizing at least a portion of the patient support with a compressible medium in response to a control signal, generating a pressure signal in response to a pressure of the compressible medium within the patient support, measuring a weight of the patient on the patient support, and generating the control signal in response to the pressure signal and the measured patient weight.

According to another illustrative embodiment of the present invention, an apparatus for supporting a patient is provided. The apparatus comprises a base, a frame, a patient support coupled to the frame, and a lift mechanism coupled to the base and the frame. The lift mechanism is configured to selectably elevate a first end of the patient support relative to a second end of the patient support. A force sensor is coupled to the patient support and is configured to generate a force signal in response to a detected force. The apparatus further comprises an angle sensor coupled to one of the frame and the patient support, the angle sensor being configured to generate an angle signal in response to an angle of the force sensor. A controller is coupled to the angle sensor to receive the angle signal therefrom and is coupled to the force sensor to receive the force signal therefrom. The controller is configured to generate a weight signal in response to the angle signal and the force signal. An output device is coupled to the controller to receive the weight signal therefrom and is configured to indicate a weight of the patient based on the weight signal.

According to another illustrative embodiment of the present invention, a method for supporting a patient on a patient support is provided. The patient support includes a first end and a second end. The patient has a mass accelerated by gravity to produce a weight force having a vertical direction. The weight force is conceivable as a sum of component vector forces including a first force vector and a second force vector. The first force vector has a first magnitude directed in a first direction at an angle relative to the direction of the weight force. The second force vector has a second magnitude directed in a second direction perpendicular to the first direction. The method comprises the steps of supporting the patient on the patient support, selectably elevating the first end of the patient support relative to the second end of the patient support, measuring an angle of the patient support, generating a weight signal in response to the angle of the first force vector and the first magnitude, and providing an indication of the weight signal.

According to another illustrative embodiment of the present invention, a method of supporting a patient on a patient support having at least one fluid-filled zone is provided. The method comprises the steps of detecting an actual pressure within the fluid-filled zone, measuring a weight of the patient on the patient support, and comparing the actual pressure within the fluid-filled zone to an optimum pressure of the fluid-filled zone based upon the measured patient weight. The method further comprises the step of adjusting the pressure within the fluid-filled zone, if necessary, based on the patient weight.

According to another illustrative embodiment of the present invention, a method of determining a weight of a patient located on a movable patient support is provided. The method comprising the steps of providing a scale to determine a weight value of the patient, determining an angle of the patient support, and adjusting the weight value detected by the scale based on the angle of the patient support.

A further illustrative embodiment of the present invention provides a method for determining and setting pressures for cushions or sections of a patient support. The method comprises the steps of measuring force exerted upon a seat section of the patient support and measuring an angle that a head section of the patient support assumes relative to horizontal. The method further comprises the steps of calculating the weight of a patient from the seat force measurement and the head section angle measurement. The method also comprises the steps of determining baseline pressure values of the sections based upon the calculated weight of the patient, and setting pressures in the sections to the determined baseline pressure values.

A further illustrative embodiment of the present invention provides a method of determining and setting pressures for cushions or sections of a patient support. The method comprises the steps of measuring force exerted upon a seat section of the patient support and measuring the angle that a head section of the patient support assumes relative to horizontal. The method further comprises the steps of comparing the force measurement and angle measurement to a set of predetermined values in a comparison table and determining the weight of a patient therefrom. The method also comprises the steps of determining baseline pressure values of the sections based upon the determined weight of the patient, and setting baseline pressures in the sections to the determined baseline pressure values.

Another illustrative embodiment of the present invention provides a patient support comprising a frame, and a deck supported by the frame having head, seat, and foot sections configured to articulate relative to each other. An inflatable mattress is supported by the deck and includes head, seat, and foot sections positioned above the head, seat, and foot sections of the deck. The patient support further comprises a force sensor configured to sense the force applied to the seat section of the mattress and an angle sensor configured to sense the angle of the head section of the deck relative to horizontal. The patient support also comprises a controller configured to receive input from the force sensor and the angle sensor and to determine the weight of a patient upon the patient support, the controller being further configured to determine baseline pressures for the sections of the mattress.

A further illustrative embodiment of the present invention provides a method of controlling a patient support having at least one fluid-filled zone. The method comprises the steps of detecting an actual pressure within the fluid-filled zone, providing a first force sensor configured to measure force applied to the patient support, and determining a first measured weight of a patient supported on the patient support from the first force sensor. The method further comprises the step of setting a baseline pressure within the fluid-filled zone based upon the first measured weight. The method also comprises the steps of providing a second force sensor configured to measure force applied to the patient support, determining a second measured weight of the patient from the second force sensor, and comparing the first measured weight to the second measured weight. The method further comprises the step of providing a diagnostic output if a differential between the first measured weight and the second measured weight exceeds a predetermined value.

Another illustrative embodiment of the present invention provides a patient support comprising a frame, a deck supported by the frame, and a first force sensor operably coupled to the deck and configured to provide a first force output indicative of force applied to the deck. A mattress is supported by the deck and includes a fluid-filled seat section. A second force sensor is operably coupled to the seat section of the mattress and is configured to provide a second force output indicative of force applied to the seat section. A controller is configured to receive the first force output and the second force output, the controller including a processor configured to determine a first measured weight of the patient in response to the first force output and to determine a second measured weight of the patient in response to the second force output. The processor is further configured to provide a diagnostic output if a differential between the first measured weight and the second measured weight exceeds a predetermined value.

In a further illustrative embodiment, a patient support comprises at least one deck section and at least one fluid receiving cushion coupled to the at least one deck section. A weight sensor is configured to detect the weight of a patient supported by the at least one fluid receiving cushion. An angle sensor is configured to determine an angle of the at least one deck section. A controller is configured to receive input from the weight sensor and the angle sensor and to set an inflation pressure for the at least one fluid receiving cushion.

Additional features of the invention will become apparent to those skilled in the art upon consideration of the following detailed description of illustrated embodiments exemplifying the best mode of carrying out the invention as presently perceived.

BRIEF DESCRIPTION OF THE DRAWINGS

The detailed description particularly refers to the accompanying figures in which:

FIG. 16 is an illustrative data table configured to be utilized in one embodiment of the flow chart of FIG. 15;

FIG. 17 is a further illustrative data table similar to the data table of FIG. 16 and which is configured to be utilized in another embodiment of the flow chart of FIG. 15.

DETAILED DESCRIPTION OF THE DRAWINGS

Figure 1:
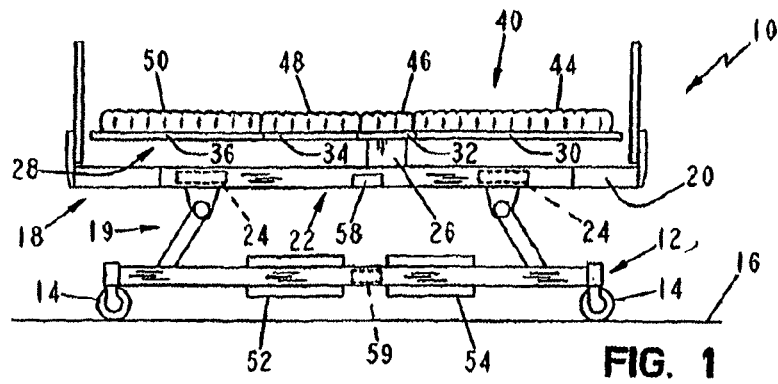
FIG. 1 is a side elevational view of a hospital bed with a scale and pressure control system according to an illustrative embodiment of the present invention.
Figure 2:
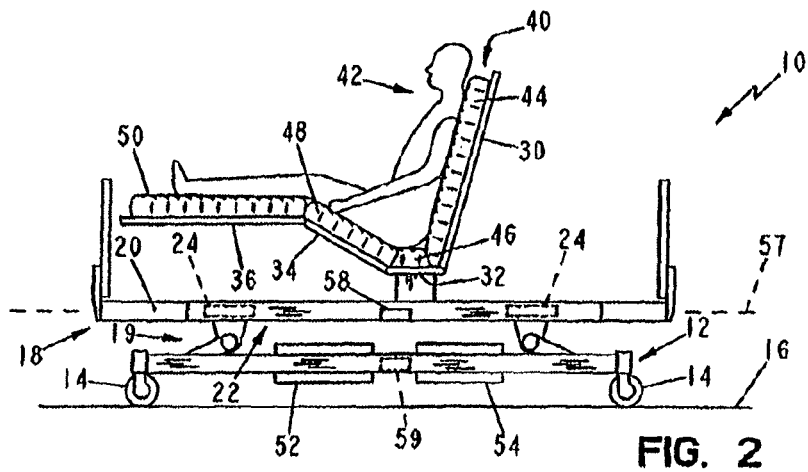
FIG. 2 is a side elevational view of the hospital bed of FIG. 1 with a support deck positioned in an articulated, sitting position.
Figure 3:
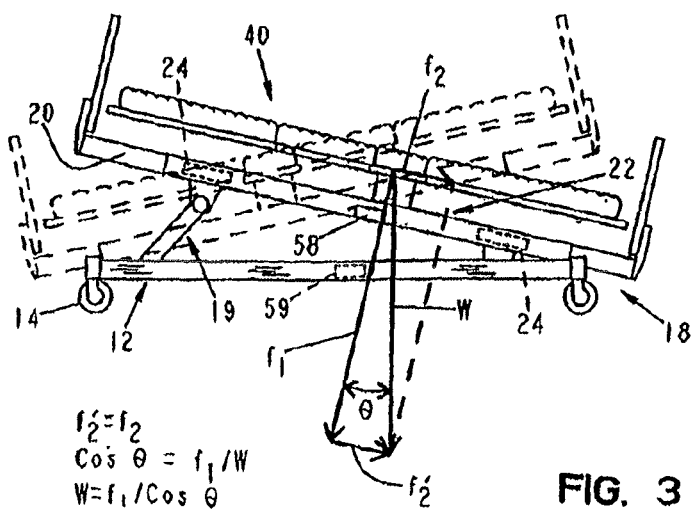
FIG. 3 is a side elevational view of the hospital bed of FIG. 1 illustrating the support deck in a Trendelenburg position (head down) in solid line and in a reverse Trendelenburg (head up) position in broken line, respectively.

Referring now to the drawings, FIG. 1-3 illustrate a hospital bed 10 of the present invention. The bed 10 illustratively includes a base 12 having a plurality of wheels or casters 14 located on a floor 16. A movable frame 18 is coupled to base 12 by a conventional lifting mechanisms 19. Frame 18 includes a support frame 20 and a weigh frame 22 coupled to support frame 20 by a plurality of load cells 24 in a conventional manner. See, for example, U.S. Pat. No. 4,953,244, which is assigned to the assignee of the present invention and is expressly incorporated herein by reference.

A support 26 is coupled to weigh frame 22. An articulating deck 28 is coupled to support 26 so that the entire weight of the deck 28 and the patient 42 thereon is supported by the weigh frame 22. In an illustrative embodiment, deck 28 includes a head deck section 30, a seat deck section 32, a thigh deck section 34, and a foot deck section 36. These deck sections 30, 32, 34 and 36 are pivotably coupled together to permit articulation of the deck 28 as illustrated in FIG. 2. Mechanisms for moving the various deck sections 30, 32, 34 and 36 are well known in the art.

A patient support 40 such as a fluid filled mattress is located on the deck 28 to support the patient 42. Illustratively, the patient support 40 includes a head zone 44, a seat zone 46, a thigh zone 48, and a foot zone 50. In an illustrated embodiment, the head zone 44, seat zone 46, thigh zone 48, and foot zone 50 are independently pressurizable zones.

A fluid supply 52 and a controller 54 are illustratively coupled to base 12 and to the various zones 44, 46, 48 and 50 of patient support 40 in a conventional manner. Controller 54 therefore adjusts the pressure within the zones 44, 46, 48 and 50 based on the desired pressure setting characteristics for supporting patient 42. In an illustrated embodiment, fluid supply 52 is a blower or compressor used to fill the patient support zones 44, 46, 48, 50 with air, although other types of fluid may be used.

As discussed above, frame 18 is pivotally coupled to lifting mechanisms 19, which are in turn pivotally coupled to base 12. In a manner which is well-known in the art, lifting mechanisms 19 provide general raising and lowering of frame 18 relative to base 12. Further, lifting mechanisms 19 provide for positioning of frame 18 (and thus, also patient support deck 28) in Trendelenburg (head down) or reverse Trendelenburg (head up) orientations as shown in FIG. 3. Such types of hospital bed configurations are well-known. In any event, it should be appreciated that the specific lifting mechanisms 19 disclosed herein are merely exemplary and not limiting to the present invention.

When a patient (not shown in FIG. 3) rests on patient support 40, the patient's mass is accelerated by gravity to produce a weight force W directed in a vertical, downward direction. When the deck 28 is aligned in a non-parallel or non-horizontal orientation relative to the floor 16, as shown in FIG. 3, the weight force W is conceivable as a sum of component vector forces including a force vector $f_1$ perpendicular to the weigh frame 22 and a second force vector $f_2$ parallel to the weigh frame 22. It should be appreciated, then, that first force vector $f_1$ has a first magnitude directed at a force angle θ relative to the direction of the weight force W and second force vector $f_2$ has a second magnitude that is directed perpendicular to the direction of first force $f_1$. To this end, it should be readily appreciated that force angle θ is a complement of the angle between vertical and the plane of seat section 58.

Load cells 24 typically measure only forces which are applied perpendicularly to the weigh frame 22, such as force vector $f_1$. Therefore, when a load cell 24 or any other suitable force sensor is positioned to measure and indicate the first force vector $f_1$ as the weight of the patient, the measured weight of the patient is inaccurate when the weigh frame 22 is in a Trendelenburg position, a reverse Trendelenburg position, or other angled (non-horizontal) position because the weight force W is not perpendicular to the force sensor. However, FIG. 3 shows that:

$$\cos\theta = f_1/W$$

and, therefore $$W = f_1/\cos\theta$$

As a result, a measurement of the force angle θ (and a determination of the cosine the force angle θ) is used to compensate a measurement of the first force $f_1$ in order to arrive at an actual weight force W (that is, the actual weight of the patient) when the angle of inclination of the weight frame 22 is non-horizontal, typically between the Trendelenburg and reverse Trendelenburg positions.

As discussed below, the present invention provides an angle sensor 58 coupled to movable frame 18 to provide an indication of the angle of the frame. As discussed below, angle sensor 58 is illustratively an accelerometer, although other sensors may be used. In one illustrated embodiment, the accelerometer is a conventional dual-axis accelerometer. In other words, the angle sensor 58 detects the angle of the movable frame 18 when it is pivoted about a transverse axis such as shown in FIG. 3. In addition, the angle sensor 58 provides an output signal indicating the angle of movement of movable frame 18 about a longitudinal axis 59 such as during rotational therapy of the patient 42. See, for example, U.S. Pat. No. 6,282,736 which is assigned to the assignee of the present invention and is incorporated herein by reference. As discussed below, a controller uses output signals from the angle sensor 58 to compensate for the errors created when the movable frame 18 is aligned at a non-horizontal angle.

In another embodiment of the present invention, a second angle sensor 59 is placed on base frame 12. In this embodiment, a compensation may be made for unlevel floor 16 to further improve accuracy of the corrected weight signal.

Figure 4:
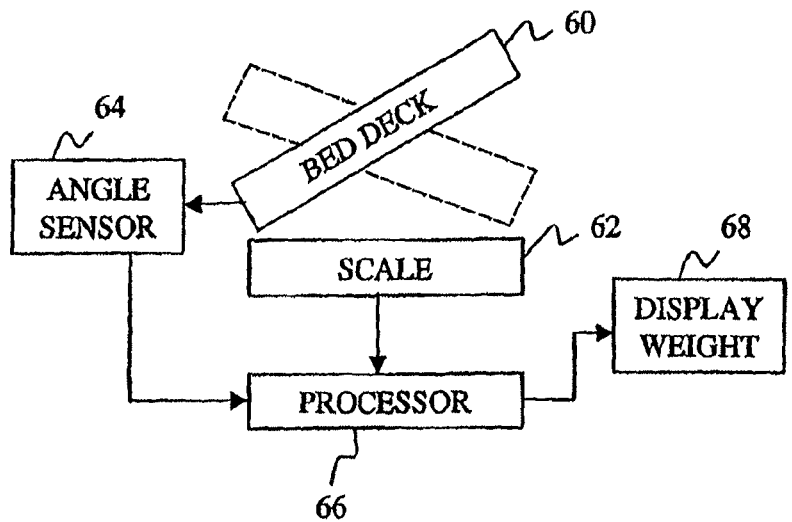
FIG. 4 is a block diagram illustrating the bed scale apparatus which compensates for an angle of a movable support frame to provide an accurate patient weight reading.

FIG. 4 is a diagrammatical view of an embodiment of the invention. A bed has a bed deck and support frame 60 which are movable to a plurality of angled positions as discussed above. Also as discussed above, hospital beds typically have a scale 62 such as a series of load cells located beneath a weigh frame. This scale 62 allows caregivers to weigh patients without making them leave the bed. Many hospital beds permit adjustment of a patient support deck and frame 60 from a normal horizontal position to angled head down or head up position—called Trendelenburg and reverse Trendelenburg positions. When the bed deck and frame 60 are aligned at an angle, the measured weight of the patient on the bed is inaccurate due to a cosine error since the load is not perpendicular to the load cells as discussed above.

Therefore, an angle sensor 64 is coupled to bed deck and/or frame 60. Inputs from angle sensor 64 and bed scale 62 are received by processor 66. An output from processor 66 generates weight output on a display 68. Angle sensor 64 measures the angle of bed deck and frame 60 and outputs a signal corresponding to the angle. Bed scale 62 measures the weight of the bed deck 60 and the patient and outputs a corresponding signal. Processor 66 uses input signals from angle sensor 64 and bed scale 62 to compensate for error introduced in the scale reading when the bed deck 60 is aligned at an angle using the formula discussed above and in more detail below. The processor 66 outputs the corrected patient weight to weight display 68.

Figure 5:
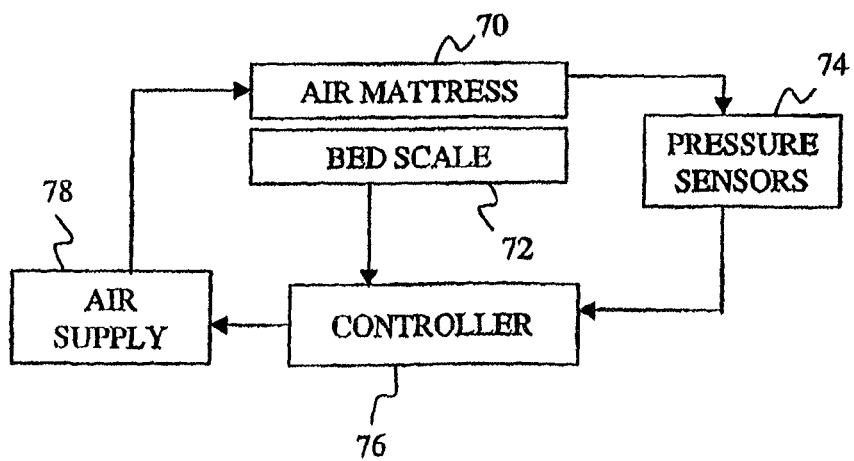
FIG. 5 is a block diagram illustrating another illustrative embodiment of the invention which continuously adjusts pressure within a patient support based upon an input signal from a bed scale.

In another embodiment of the present invention, diagrammatically illustrated in FIG. 5, a hospital bed 10 has a controller which automatically adjusts pressure within a patient support 70 based on a continuous feedback from a scale 72. As discussed above, scale 72 allows caregivers to weigh patients without making them leave the bed 10. Often the patient's weight is a factor considered when determining optimum air pressure in an air mattress 70 for different size patients. Conventional controllers are generally programmed with several weight ranges and corresponding mattress pressures that make the patient more comfortable and reduce pressure on the patient's skin. Usually the caregiver inputs the weight of the patient, or presses a button corresponding to a weight range of the patient, and the controller then maintains a predetermined pressure in the air mattress based on the input weight.

In the illustrated embodiment, pressure sensors 74 measure the air pressure in various zones of air mattress 70. An output of pressure sensors 74 and the output of bed scale 72 are input into controller 76. Controller 76 uses the input signals from bed scale 72 to determine the optimum pressure of zones of the air mattress 70 automatically. Controller 76 uses the input signals from pressure sensors 74 to determine whether the pressure in air mattress 70 needs adjustment. The output from controller 76 to air supply 78 keeps the air mattress at the desired pressure based on the weight input signal from scale 72.

Figure 6:
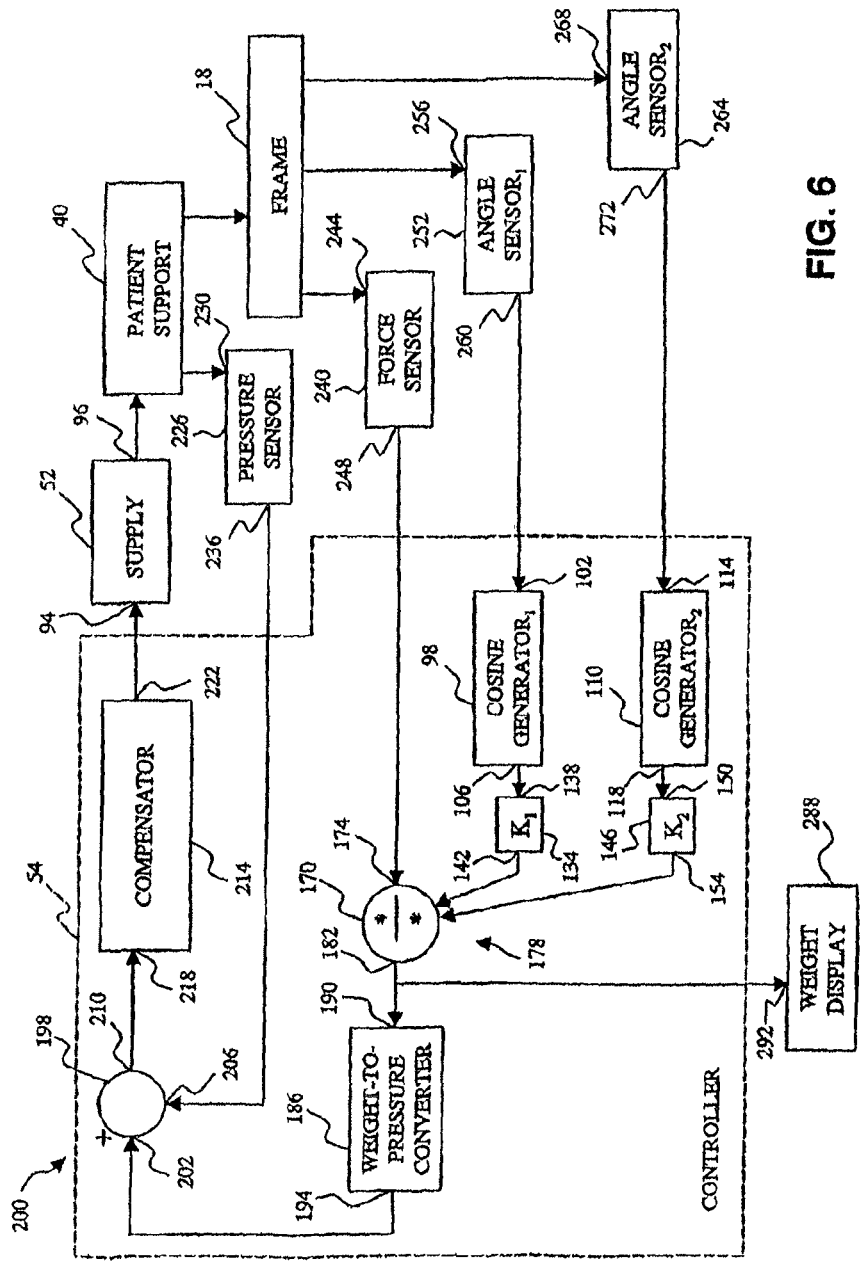
FIG. 6 is a block diagram of a patient support pressure control system according to an illustrative embodiment of the present invention.

FIG. 6 is a block diagram of an illustrated patient support pressure control system 200 according to the present invention. As noted above, in general, controller 54 and supply 52 operate to adjust one or more pressures within patient support 40 based on the weight of the patient. To this end, controller 54 is a "closed-loop" (or "feedback") type controller constructed from any of various suitable micro-controllers and suitable input-output ("I/O") devices which are well known. Further, it should be readily appreciated that the exemplary elements of controller 54 described in connection with FIG. 6 may be implemented in suitable hardware, suitable software, or any suitable combination thereof.

Supply 52 is illustratively a blower, compressor, pump or other suitable device which is configured in a well known manner to receive control signals from controller 54 and pressurize and provide the compressible medium (discussed above) independently to head zone 44, seat zone 46, thigh zone 48, and foot zone 50 of patient support 40 in response to the control signals. To this end, supply 52 may suitably include valves, pressure regulators, distribution manifolds or the like. In the exemplary embodiment of FIG. 4, supply 52 includes an input 94 and an output 96.

Controller 54 includes a first cosine generator 98 having an input 102 and an output 106, and a second optional cosine generator 110 having an input 114 and an output 118. Each of the cosine generators 98, 110 is configured to receive an angle signal (discussed further below) at its respective input and provide at its respective output a cosine signal corresponding to the cosine of the angle represented by the angle signal.

Controller 54 further includes an adjuster 134 having an input 138 and an output 142, and an optional adjuster 146 having an input 150 and an output 154. Each of the adjusters 134, 146 is configured to suitably amplify or attenuate the signal received at its respective input and provide the resulting signal at its respective output. Input 138 of adjuster 134 is coupled to output 106 of cosine generator 98 to receive the respective cosine signal (discussed above) therefrom. Input 150 of adjuster 146 is coupled to output 118 of cosine generator 110 to receive the respective cosine signal (discussed above) therefrom.

Controller 54 further includes a divider 170 having an input 174, inputs 178, and an output 182. Divider 170 is configured to receive a first signal at input 174, to receive additional signals at each of inputs 178, and to provide at output 182 a signal corresponding to a mathematical division of the signal received at input 174 by all of the signals received at inputs 178. One of inputs 178 of divider 170 is coupled to output 142 of adjuster 134 to receive the respective signal (discussed above) therefrom. Another input 178 may be coupled to output 154 of optional adjuster 146 to receive the respective signal (discussed above) therefrom.

Controller 54 further includes a converter 186 having an input 190 and an output 194. Converter 186 is configured to convert a signal representing the weight of a patient into a signal representing a desired pressure for the various zones 44, 46, 48, 50 of patient support 40. It should be appreciated that the conversion may be may be implemented by a suitable formula or formulae, a suitable lookup table, or a suitable combination thereof for determining an optimum pressure of support 40 based on the patient's weight. In any event, input 190 of converter 186 is coupled to output 182 of divider 170 to receive the respective signal (discussed above) therefrom.

Controller 54 further includes a comparator 198 having an input 202, an input 206, an output 210. Comparator 198 is configured to receive a signal at input 202, receive a signal at input 206, and provide the difference therebetween at output 210. Input 202 of comparator 198 is coupled to output 194 of converter 186 to receive the respective desired pressure signal (discussed above) therefrom, Controller 54 also includes a compensator 214 having an input 218 and an output 222. Compensator 214 is suitably configured to move closed-loop parameters of patient support pressure control system 200 into desirable ranges and to provide suitable drive signals to supply 52. Various suitable ways of implementing closed-loop control compensators are well known. Input 218 of compensator 214 is coupled to output 210 of comparator 198 to receive the respective difference signal (discussed above) therefrom. Output 222 of compensator 214 is coupled to input 94 of supply 92.

In addition to controller 54, patient support pressure control system 200 further includes at least one pressure sensor 226 having an input 230 and an output 236. Pressure sensor 226 is configured to be exposed to a pressure of the compressible medium and to generate a pressure signal corresponding thereto. To this end, it should be appreciated that pressure sensor 226 may be constructed with a suitable strain gage or in any other well known manner. Accordingly, input 230 is coupled a zone 44, 46, 48, 50 of patient support 40 to receive the pressure of the compressible medium therein, and output 236 is coupled to input 206 of comparator 198 to provide the corresponding pressure signal thereto. In the illustrated embodiment, a separate pressure sensor 226 is used for each zone 44, 46, 48, 50.

Patient support pressure control system 200 further includes a force sensor 240 having an input 244 and an output 248. Force sensor 240 is configured to detect the magnitude of the force $f_1$. To this end, force sensor 240 may be implemented with load cells or any other suitable alternative force sensing device. Further, it should be appreciated that force sensor 240 may be implemented as a plurality of individual force sensors, in which case controller 54 processes the force data to derive an aggregate or overall force signal therefrom. In any event, input 244 of force sensor 240 is coupled to weigh frame 22 to detect $f_1$. Here, it should be readily appreciated that force sensor 240 may be placed in any number of suitable locations. Output 248 of force sensor 240 is coupled to input 174 of divider 170 to provide the corresponding pressure signal thereto.

Angle sensor 252 is configured to generate an angle signal corresponding to the angle of the weigh frame 22 when pivoted about an axis transverse to the moveable frame 18 as shown in FIG. 3. Accordingly, angle sensor 252 is coupled to frame 20, weigh frame 22 on deck 28 support to detect angle θ and an output 260 that is coupled to input 102 of cosine generator 98 to provide the corresponding angle signal thereto. Angle sensor 252 may be implemented with an Orientation Systems type DX-016D-055 tilt sensor, with an Analog Devices ADXL202E accelerometer type tilt sensor, or in any other suitable manner. In any event, various devices for detecting angles using earth magnetic field, accelerometers, inclinometers, drive position monitors, etc. are well-known, and any suitable alternative may be used. Further, it should be readily appreciated that the angle sensor may be located in any number of suitable locations on bed 10.

Angle sensor 264 is configured to generate an angle signal corresponding to an angle of tilt of weigh frame 22 when the moveable frame 18 is pivoted about its longitudinal axis 59. This may be when the frame 18 is rotated to provide lateral rotational therapy to the patient 42. Angle sensor 264 is coupled to support frame 20, weigh frame 22 or deck 28 to detect the angle. An output 272 of sensor 264 is coupled to input 114 of cosine generator 110 to provide the corresponding angle signal thereto. Like angle sensor 252, angle sensor 264 may be implemented with an Orientation Systems type DX-016D-055 tilt sensor, with an Analog Devices ADXL202E tilt sensor, or in any other suitable manner, may be located in any number of suitable locations, and may be implemented as a plurality of separate angle sensors. Illustratively, a single dual axis accelerometer may be used to provide both angle sensors 260 and 264.

Patient support pressure control system 200 also includes a weight display 288 having an input 292. Weight display 288 is configure to receive a signal corresponding to the weight of the patient and to display or otherwise announce the weight value in a human readable or discernable format as is well known. Accordingly, input 292 of weight display 288 is coupled to output 182 of divider 170 to receive the weight signal therefrom. Further, it should be readily appreciated that the display or other annunciation device(s) of weight display 288 are suitably positioned on the hospital bed 10 to facilitate reading of the weight information by a user of the present invention.

Figure 7:
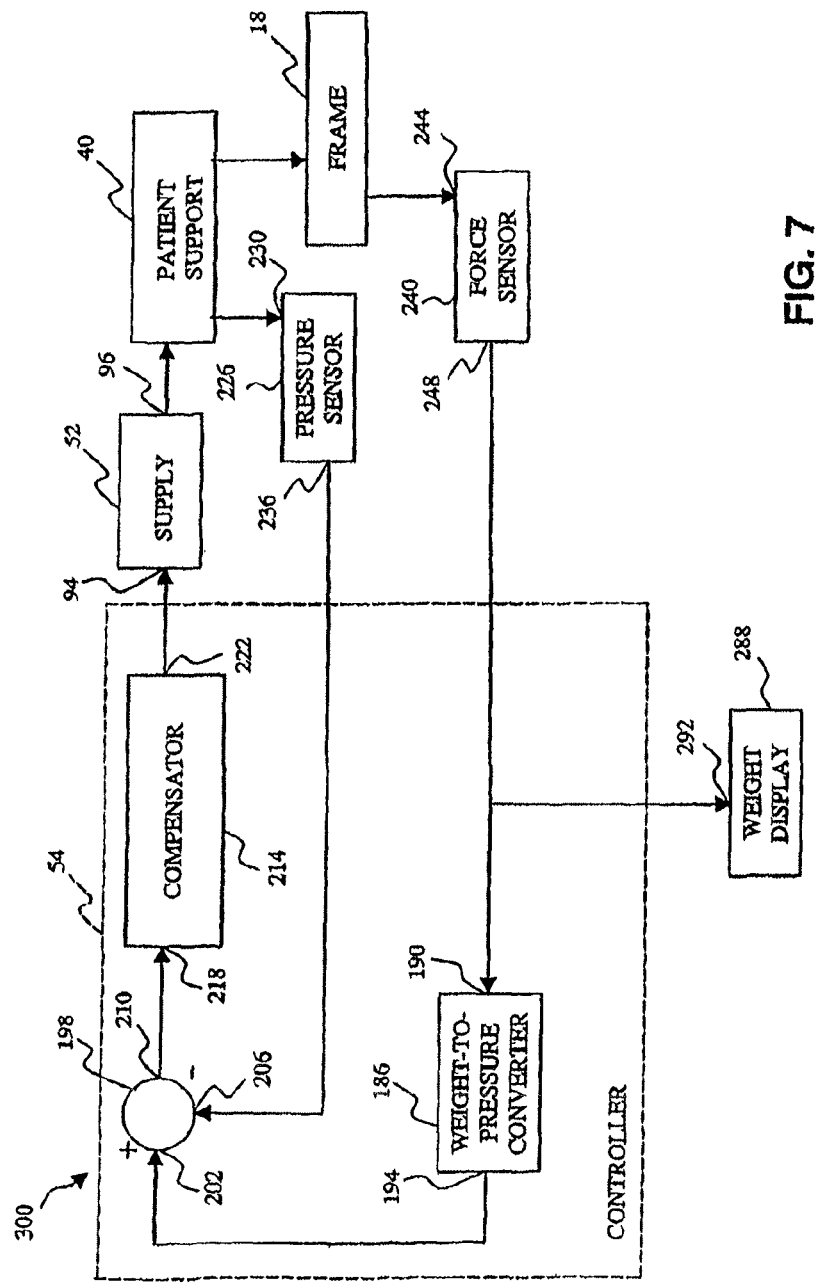
FIG. 7 is a block diagram of a pressure control system according to a further illustrative embodiment of the present invention.

FIG. 7 is a block diagram of an alternative embodiment of a pressure control system 300 according to the present invention. It should be readily appreciated that the elements of pressure control system 300 are the same as those of pressure control system 200 (discussed above in connection with FIG. 6), except pressure control system 300 does not include the angle sensors, cosine generators, adjusters, or divider. Instead, in pressure control system 300, output 248 of force sensor 240 is coupled directly to input 190 of converter 186 and input 292 of weight display 288.

Figure 8:
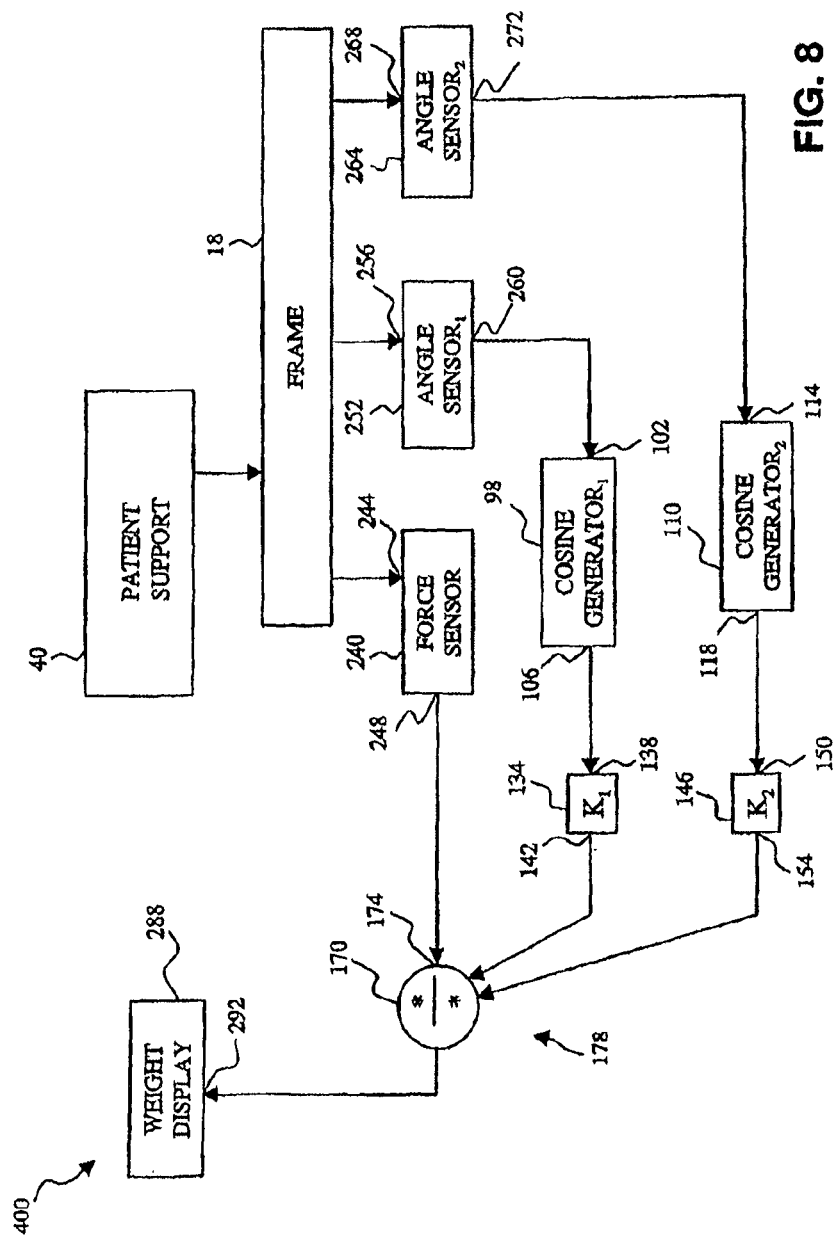
FIG. 8 is a block diagram of a weight display system according to an illustrative embodiment of the present invention.

FIG. 8 is a block diagram of a weight display system 400 according to the present invention. It should be readily appreciated that the elements of weight display system 400 are the same as those of pressure control system 200 (discussed above in connection with FIG. 6), except weight display system 400 does not "close-the-loop" through the converter, comparator, compensator, or supply.

Figure 9:
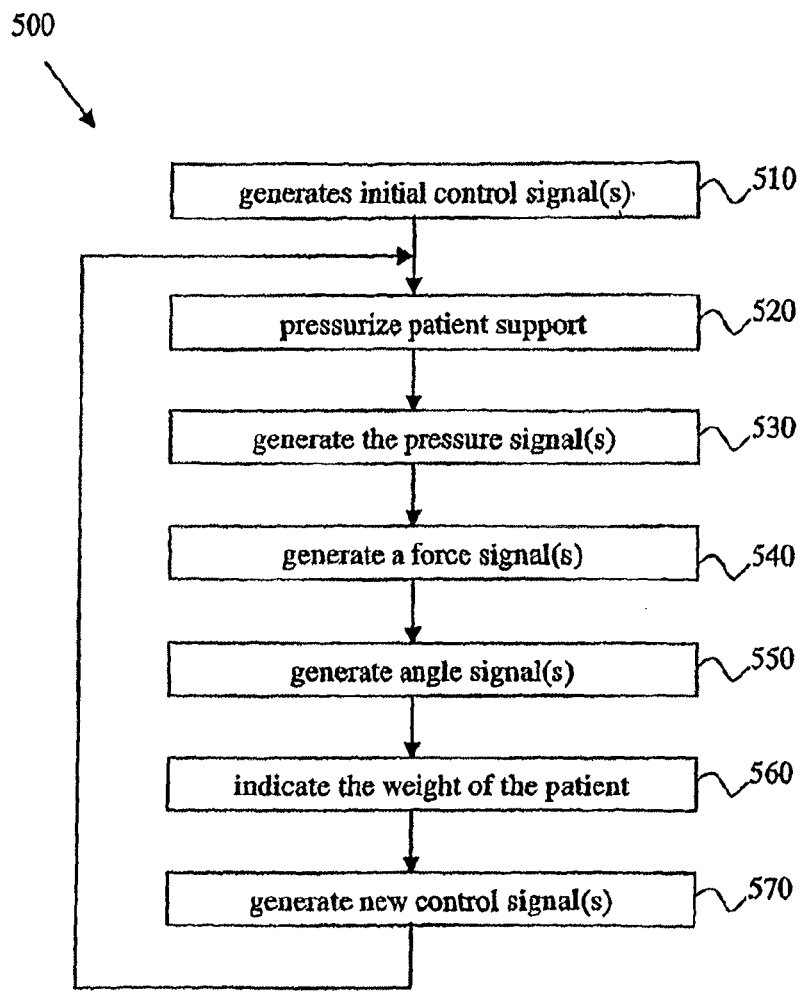
FIG. 9 is a flow diagram of an illustrative method of operation for the pressure control system of FIG. 1.

FIG. 9 is a flow diagram of a method of operation 500 for the pressure control system 200. At step 510 (startup), controller 90 generates initial control signal(s) for supply 52. At step 520, supply 52 pressurizes the zones 44, 46, 48, 50 of patient support 40 with the compressible medium in response to the control signal(s). At step 530, pressure sensor(s) 226 generates the pressure signal(s) in response to pressure(s) within patient support 40. At step 540, force sensor 240 generates a force signal(s) in response to the force f₁ (see FIG. 3, above). At step 550, angle sensor 252 (and optional angle sensor 264) generate an angle signal(s) corresponding to angle of alignment of weigh frames 22 about transverse and longitudinal axes. At step 560, weight display 288 displays or otherwise announces the weight of the patient (i.e., the weight force W in a human readable or discernable format. At step 570, controller 54 generates new control signal(s) for supply 52 in response to the pressure signal(s), the force signal(s), and a cosine of each of the angle signal(s). Steps 520-570 are repeated as necessary to maintain closed-loop control of system 200 as desired.

Thus, in operation, controller 54 automatically compensate for weight change of the patient by causing supply 52 to increase or decrease pressure within patient support 40 as necessary to maintain desired support characteristics. For the user's convenience, weight display 288 indicates the weight of the patient.

It should be appreciated that operation of pressure control system 300 is practically the same as the operation of pressure control system 200 (discussed above) except that in operation of pressure control system 300, the angles of weigh frame 22 are not factored into the closed-loop control of the pressure(s) within patient support 40.

Similarly, it should be appreciated that operation of weight display system 400 (see FIG. 8, above) is practically the same as the operation of pressure control system 200 except that in operation of weight display system 400 the closed-loop control of the pressure(s) within patient support 40 is omitted.

As detailed above, angle sensor 252 may be of conventional design and illustratively include outputs XOUT, YOUT which connect to 2 micro pins each on a microcontroller, or 4 total pins. These micro pins are PCA (programmable counter array) and are interrupt driven. This means that they capture the timing based on a falling or rising edge of the signal coming in. The micro pins generate a flag indicating new PCA values in the PCA registers. One of the XOUT/YOUT pins is set on falling edge and the other on rising edge. This way the high and low times are available (in the PCA registers) and only simple math is required to determine the duty cycle (if HIGH_TIME=LOW_TIME then the duty cycle is 50% which is level from zero).

As shown in FIGS. 10-13, a further illustrative hospital bed 1010 is provided including a frame 1012 positioned on the floor 1013, a deck 1014 coupled to the frame 1012, a mattress 1016 positioned on the deck 1014, a headboard 1018 coupled to the frame 1012, a footboard 1020 coupled to the deck 1014, and siderails 1022, 1024 coupled to deck 1014.

Frame 1012 is configured to raise and lower the deck 1014 relative to the floor 1013, while the deck 1014 is configured to articulate to a plurality of positions. The deck 1014 includes a head section 1026 hingedly connected to a seat section 1028 that is hingedly connected to a foot section 1030. The frame 1012 and deck 1014 may be of the type disclosed in U.S. Pat. No. 5,715,548, which is assigned to the assignee of the present invention and the disclosure of which is expressly incorporated herein by reference.

The mattress 1016 includes a plurality of sections or zones, illustratively a head section 1032, a seat section 1034, and a foot section 1036 associated with corresponding sections 1026, 1028, and 1030 of the frame 1014. More particularly, each mattress section 1032, 1034, and 1036 is supported by, coupled to, and articulates with the corresponding deck section 1026, 1028, and 1030. Each mattress section 1032, 1034, and 1036 is comprised of at least one corresponding air bladder or cushion 1040, 1042, and 1044 configured to be customizable by inflating to different pressures.

As described above, typically the patient's weight is a factor considered when determining optimum air pressure in an air mattress for different size patients. Conventional controllers are generally programmed with several weight ranges and corresponding mattress pressures that make the patient more comfortable and reduce pressure on the patient's skin. Usually the caregiver inputs the weight of the patient, or presses a button corresponding to a weight range of the patient, and the controller then maintains a predetermined pressure in the air mattress based on the input weight.

Figure 13:
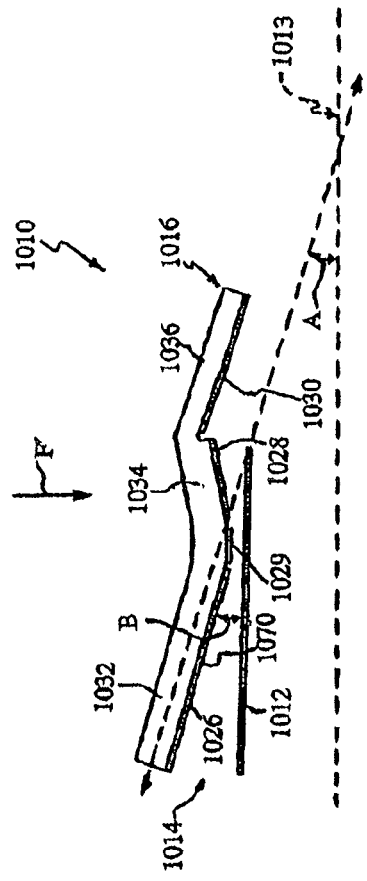
FIG. 13 is a view similar to FIG. 12 illustrating a head section of the mattress and a head section of the deck moved to any upwardly pivoted elevated position.
Figure 14:
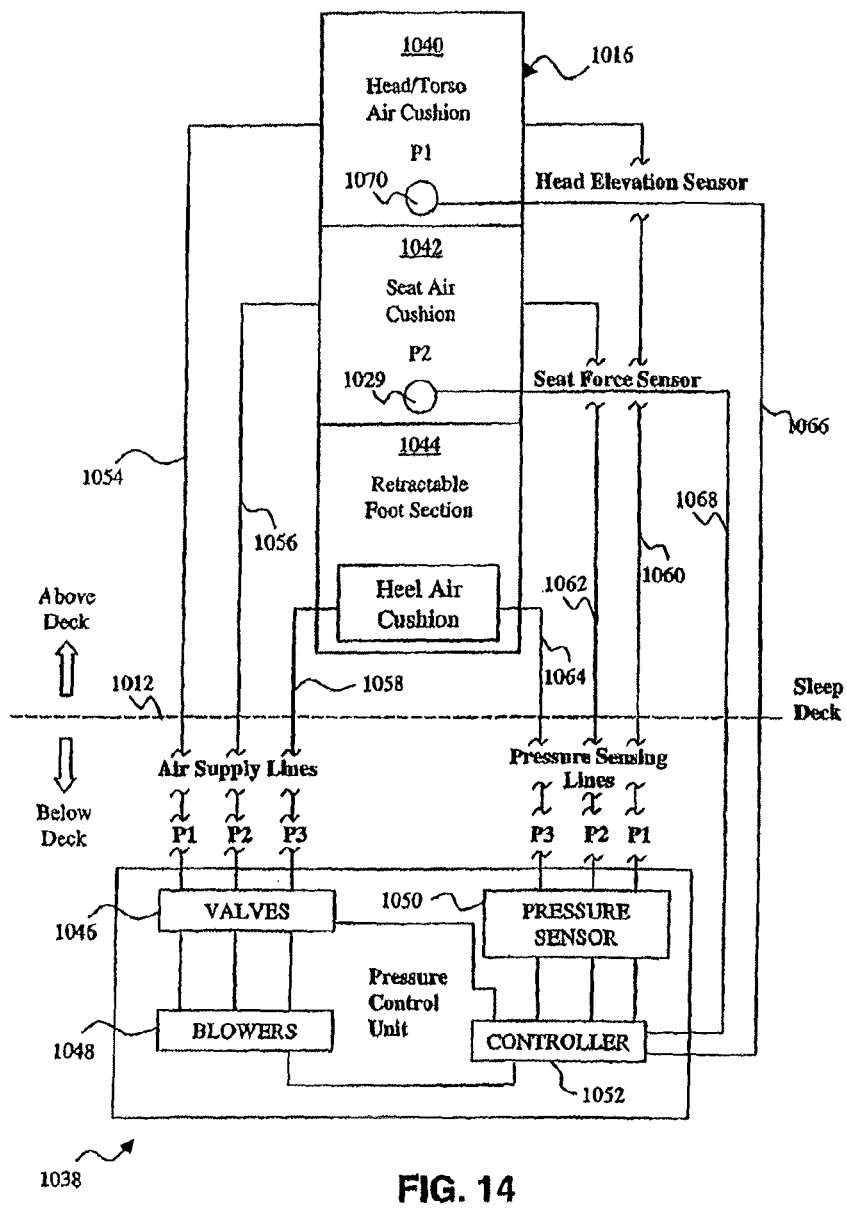
FIG. 14 is a block diagram of an illustrative mattress control system, including a pressure control apparatus, for supplying fluid to a plurality of bladders within the mattress.

As shown in FIGS. 13 and 14 of the illustrative embodiment, a seat force sensor 1029 is coupled to the seat section 1028 of the deck 1014. Illustratively, the seat force sensor 1029 is positioned intermediate the deck 1014 and the mattress 1016 and is configured to detect force or weight applied to the seat section 1034 of the mattress 1016 and output an electrical signal indicative of the detected force. Illustratively, the seat force sensor 1029 comprises a resistive pressure sensor, although other weight sensors including piezoelectric and capacitor sensors may be substituted therefore.

As shown in FIG. 14, a pressure control unit 1038 is coupled to the mattress 1016 to independently control the pressures within the air cushions 1040, 1042, and 1044. The pressure control unit 1038 is illustratively comprised of valves 1046 that regulate the air supplied to the air cushions 1040, 1042, and 1044, pumps or blowers 1048 that pressurize the air to be sent to the air cushions 1040, 1042, and 1044, pressure sensors 1050 configured to measure the pressure within the air cushions 1040, 1042, and 1044, and a controller 1052 configured to determine whether, and to what extent, the pressures within the air cushions 1040, 1042, and 1044 require adjustment. The pressure control unit 1038 is fluidly connected to the mattress 1016 by air supply hoses 1054, 1056, and 1058, and pressure sensor hoses 1060, 1062, and 1064. The pressure control until 1038 is electrically connected to the bed 1010 by electrical leads, including a head elevation lead 1066, and a seat force lead 1068.

The head air cushion 1040 is fluidly coupled via the first air supply hose 1054 to the valves 1046 such that the air supply hose 1054 is configured to transfer increases or decreases in pressure from the valves 1046 to the head air cushion 1040. Seat air cushion 1042 and foot air cushion 1044 are similarly fluidly coupled to the valves 1046 by second and third air supply hoses 1056 and 1058. The valves 1046 allow for the pressure within each cushion 1040, 1042, and 1044 to be independently controlled. Pressure may be decreased by the valve 1046 releasing pressure to atmosphere. Pressure may be increased by supplying air from the blowers 1048 through the valves 1046, the supply lines 1054, 1056, and 1058 and to the air cushions 1040, 1042, and 1044, respectively. Again, it should be appreciated that each air cushion 1040, 1042, and 1044 is configured to be independently pressurized such that pressurization of one cushion 1040, 1042, or 1044 does not necessitate pressurization of the other cushions 1040, 1042, and 1044. Further, pressurization of one cushion 1040, 1042, or 1044 may occur simultaneously with the depressurization of another cushion 1040, 1042, or 1044. In additional illustrative embodiments, a first cushion 1040, 1042, or 1044 may be depressurized by the valves 1046 diverting pressure from the first cushion 1040, 1042, or 1044 to a second cushion 1040, 1042, or 1044, thereby increasing the pressure of the second cushion 1040, 1042, or 1044. An appropriate manifold (not shown) may be utilized to interconnect the air supply hoses 1054, 1056, and 1058 through the valves 1046.

Operation of the valves 1046 and blowers 1048 is controlled by the controller 1052. The controller 1052 is preferably electrically coupled to the valves 1046 and blowers

1048. The controller 1052 is also electrically coupled to the pressure sensors 1050, the seat force sensor 1029 by the seat force lead 1068, and to a head elevation sensor 1070 by the head elevation lead 1066. The pressure sensors 1050 are coupled to the head, seat, and foot air cushions 1040, 1042, and 1044 to sense the pressure of the air received therein and may be of conventional design.

In the embodiment illustrated in FIG. 14, the pressure sensors 1050 are internal to the pressure control unit 1038 and connected to the air cushions 1040, 1042, and 1044 via hoses 1060, 1062, and 1064. However, it should be appreciated that the pressure sensors 1050 may be positioned external to the pressure control unit 1038. In one such illustrative embodiment, electrical leads run from the pressure sensors 1050, located at the respective air cushions 1040, 1042, and 1044, to the controller 1052, located within the pressure control unit 1038.

As shown in FIG. 13, the head elevation sensor 1070 is configured to measure the angle (A) that the head section 1026 of the deck 1014 forms relative to the floor upon which the bed is placed. As such, the head elevation sensor 1070 is configured to measure the angle (A) of the head section 1026 relative to a substantially horizontal plane. Alternatively, the head elevation sensor 1070 may be configured to measure the angle (B) that the head section 1026 of the deck 1014 forms relative to the frame 1012. While normally the angles (A) and (B) are substantially the same, some variations will exist if the frame 1012 is tilted relative to horizontal. In an illustrative embodiment of the present invention, a frame angle sensor (not shown) may be associated with the frame 1012 for measuring an angle of the frame 1012 relative to horizontal. As such, compensation may be made for tilting of the frame 1012 from horizontal when measuring the angle (B) between the head section 1026 and the frame 1012. The measurement from the head elevation sensor 1070 is relayed to the controller 1052 via the head elevation lead 1066.

The head elevation sensor 1070 may comprise any conventional device configured to detect angles including devices using earth magnetic field, accelerometers, inclinometers, drive position monitors, etc. Further, it should be appreciated that the head elevation sensor 1070 may be located in any number of suitable locations on the bed 1010. Illustratively, the head elevation sensor 1070 may comprise an Orientation Systems type DX-016D-055 tilt sensor of the type described above.

The seat force sensor 1029 is configured to measure the weight supported by the seat section 1028 of the deck 1014. This measurement (F') is relayed to the controller 1052 via the seat force lead 1068.

The controller 1052 receives input from the head elevation sensor 1070 and the seat force sensor 1029 to determine the weight (W) of the patient upon the bed 1010. The controller 1052 then determines, based upon the patient weight (W), the proper baseline pressures P1, P2, and P3 for the air cushions 1040, 1042, and 1044. The determination of the weight (W) and proper baseline pressures P1, P2, and P3 is illustratively performed by placing the inputs into predetermined formulas or algorithms to calculate the weight (W) and the baseline pressures P1, P2, and P3. In other embodiments, weight (W) and pressure determinations P1, P2, and P3 are performed by comparing the inputs to stored lookup or comparison tables 1078 and 1080 that output the weight (W) and the baseline pressures P1, P2, and P3. As explained below, details of the algorithms and values of the lookup tables 1078 and 1080 may be determined based upon patient characteristics and needs.

The pressures P1, P2, and P3 output by the controller 1052 are then compared to the pressures in the cushions 1040, 1042, and 1044 as sensed by the pressure sensors 1050. The controller 1052 next communicates with the blowers 1048 and valves 1046 to alter the cushion pressures to the pressures output by the controller 1052, as necessary. In an illustrative embodiment, the controller 1052 further monitors the seat force (F') and alters the cushion pressures in response to changes in the seat force.

Figure 15:
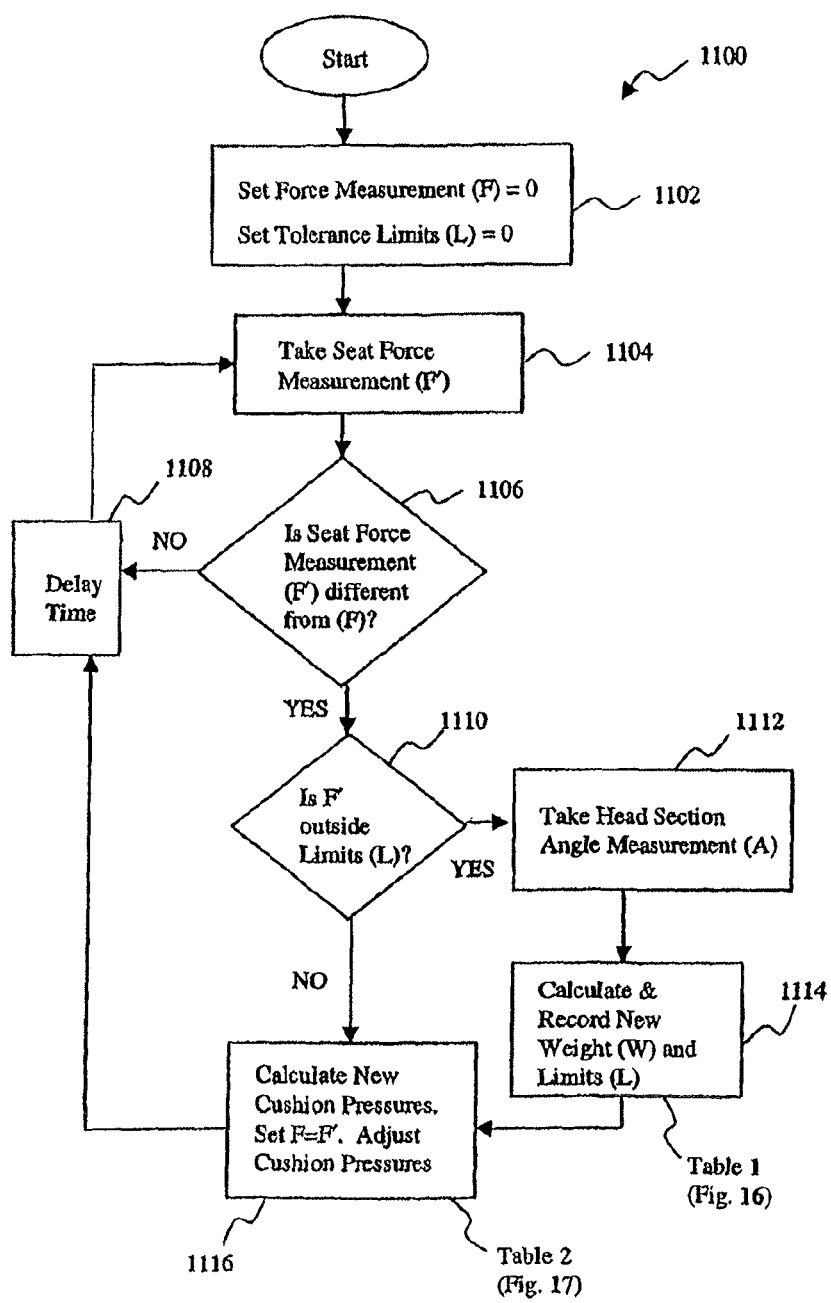
FIG. 15 is a flow chart illustrating the steps performed by the controller of the pressure control apparatus of FIG. 14.

FIG. 15 is a flowchart 1100 of the illustrative method (F') performed by the controller 1052. When the bed 1010 is powered up, the controller 1052 starts at step 1102 by initializing the values for recorded force (F) and tolerance limit (L) to zero. The controller 1052 proceeds to step 1104 and receives a patient weight measurement (F') from the seat force sensor 1029. The next step 1106 is to compare (F') to (F). If (F') equals (F), in the initial case meaning that there is no patient within the bed 1010, the controller 1052 cycles through a delay time at block 1108, and then takes another seat force measurement at block 1104. It should be appreciated that the delay time at block 1108 can be set to very small intervals such that the cycle back to taking another force measurement at block 1104 can be essentially instantaneous and provide for a substantially constant updating of the seat force measurement (F').

However, in the event that the seat force (F') is not equal to the recorded force (F), the controller 1052 proceeds to the limit comparing step 1110. The limit comparing step 1110 compares the measured seat force (F') to the tolerance limits (L). Tolerance limits (L) are usually end values of a range of forces that could typically be expected to be produced by a patient with weight (W). During the initial run-through, the weight (W) has not been yet determined, therefore, as the tolerance limits (L) were set to zero in step 1102, the new force (F') is necessarily outside of the limits (L). The force measurement (F') is usually only outside of the limits (L) on four occasions: 1) when powered up for the first time, 2) when a second person, such as a visiting relative, sits or otherwise adds weight to the seat section, 3) when the patient leaves the bed, or 4) when the patient gets in the bed.

When the force (F') is outside of the limits (L), the controller 1052 proceeds to the head angle measurement step 1112. In the measurement step 1112, the controller 1052 takes input (A) from the head elevation sensor 1070. The controller 1052 then proceeds to the calculation step 1114.

The calculation step 1114 involves the controller 1052 taking the input of the head angle (A) and the seat force measurement (F') to determine the weight (W) and the limits (L) of the range of force measurements associated with the weight (W). This determination is illustratively performed by utilizing the input in algorithms or through the use of a lookup table similar to that illustrated as Table 1 (1078) in FIG. 16.

The controller 1052 then proceeds to calculation step 1116. The calculated weight (W) is taken alone, or in combination with the force measurement (F'), to determine the baseline air cushion pressures P1, P2, and P3. Again, this determination may be performed by using an algorithm or through a lookup table similar to that illustrative as Table 2 (1080) in FIG. 17. The force measurement (F') is next recorded or stored as the current force (F). The controller 1052 communicates with the valves 1046 and blowers 1048 to set each of the air cushions 1040, 1042, and 1044 to the respective baseline pressures P1, P2, and P3.

After the controller 1052 waits out the delay time 1108, another seat force measurement (F') is taken in step 1104. The controller 1052 then proceeds to step 1106. If the patient has shifted within the bed 1010 or the angle of the head section 1026 has been altered, the measured seat force (F') will be different but typically still within the tolerance limits (L). Therefore, when a patient shifts his weight the question of step 1106 is typically answered yes and step 1110 is typically answered no. This causes controller 1052 to proceed to step 1116. Step 1116 takes the new seat force measurement (F'), alone or in combination with the previously determined weight (W), and calculates new air cushion pressures P1, P2, and P3 and adjusts the air cushions 1040, 1042, and 1044 to the new pressures P1, P2, and P3. Also, step 1116 sets and stores the new seat force (F') as the current force (F). The controller 1052 then proceeds to step 1104 after the delay time 1108.

In an alternative embodiment, if the query of decision block 1110 is answered no, meaning that the measured seat force (F') is within the limits (L), the process may proceed directly to the delay time block 1108. As such, the controller 1052 would not calculate new pressures P1, P2, and P3 nor adjust the pressures in the air cushions 1040, 1042, and 1044 in response thereto. In other words, the controller 1052 would adjust pressures within the air cushions 1040, 1042, and 1044 only when the seat force measurement (F') is outside of the limits (L).

Figure 10:
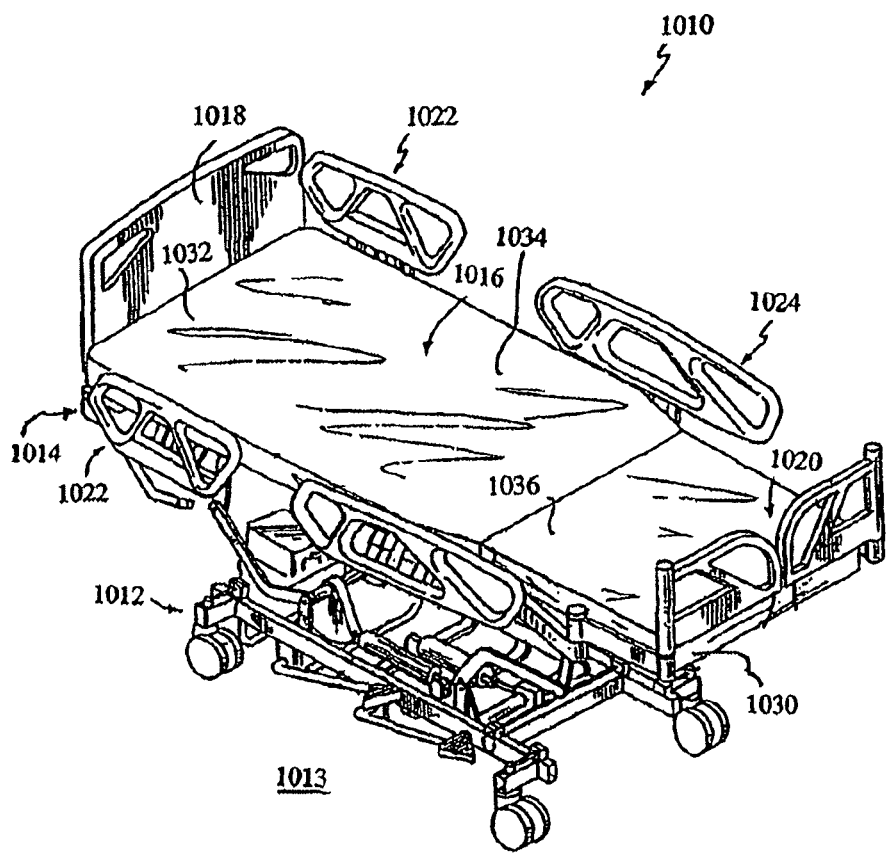
FIG. 10 is a perspective view of another illustrative embodiment bed of the present invention showing a head section of an articulating deck positioned in a horizontal position aligned at a zero degree angle relative to a frame.
Figure 12:
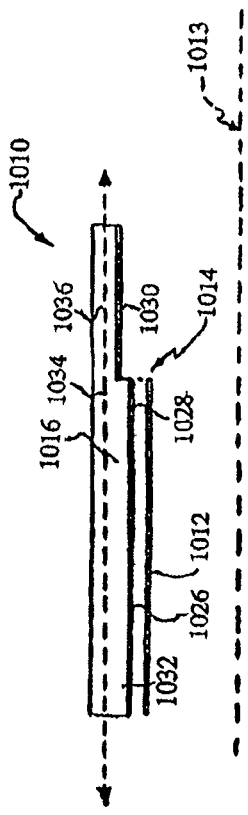
FIG. 12 is a side view of the mattress and deck of FIG. 10 in the horizontal position.

As shown in FIGS. 10 and 12, when the bed 1010 is in a fully reclined position, the head elevation sensor 1070 outputs an angle value (A) of substantially zero degrees. Therefore, in step 1114 when determining the weight (W), the controller 1052 takes the measurement from the seat force sensor 1029 and the head section angle of zero to determine the weight (W).

Figure 11:
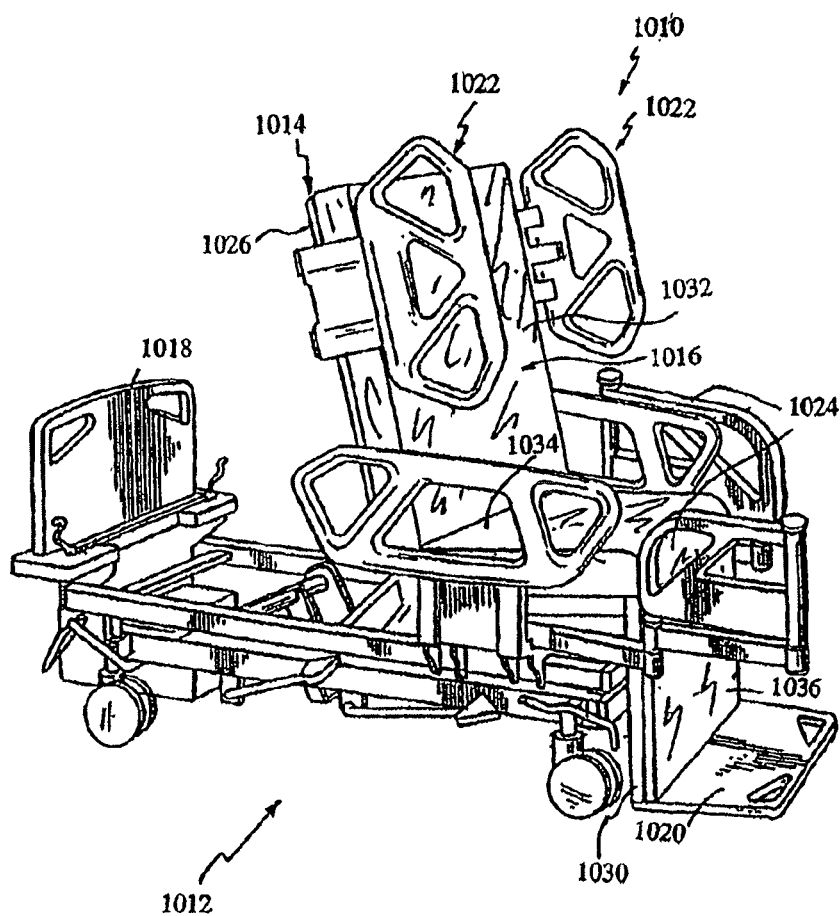
FIG. 11 is a view similar to FIG. 10 illustrating the bed with a head section of the articulating deck moved upwardly to an elevated position, a seat section of the deck inclined slightly upwardly, and a foot section of the deck moved to a generally vertical downwardly extending position.

The weight algorithm and values of Table 1 (1078, FIG. 16) are determined from known anthropometrical relationships and physics. When the head section angle (A) is equal to zero, anthropometrical relationships allow the controller 1052 to determine the overall weight based upon the weight supported by the seat section 1028 and known body mass relationships. When, as shown in FIGS. 11 and 13 the head section 1026 assumes an angle (A) relative to the horizontal floor 1013 at the time of weight (W) calculation, physics states that some of the weight normally supported by the head section 1026 when the head section 1026 is lying flat will come to bear upon the seat section 1028. Therefore, anthropometrical relationships along with physics are used to determine the weight (W) of the patient.

Further, as the patient shifts positions and adjusts the angle of the head section, the force upon the seat section (F') changes, but the weight (W) of the patient does not. Therefore, as the force upon the seat section (F') changes within the limits (L), the controller 1052 follows steps 1104, 1106, 1110, and 1116 and makes small changes to the pressures P1, P2, and P3 of the air cushions 1040, 1042, and 1044 to compensate for the shift of weight. Alternatively, as noted above, such changes may be ignored by the controller 1052 in order to avoid making such small changes to the pressures P1, P2, and P3.

Figure 18:
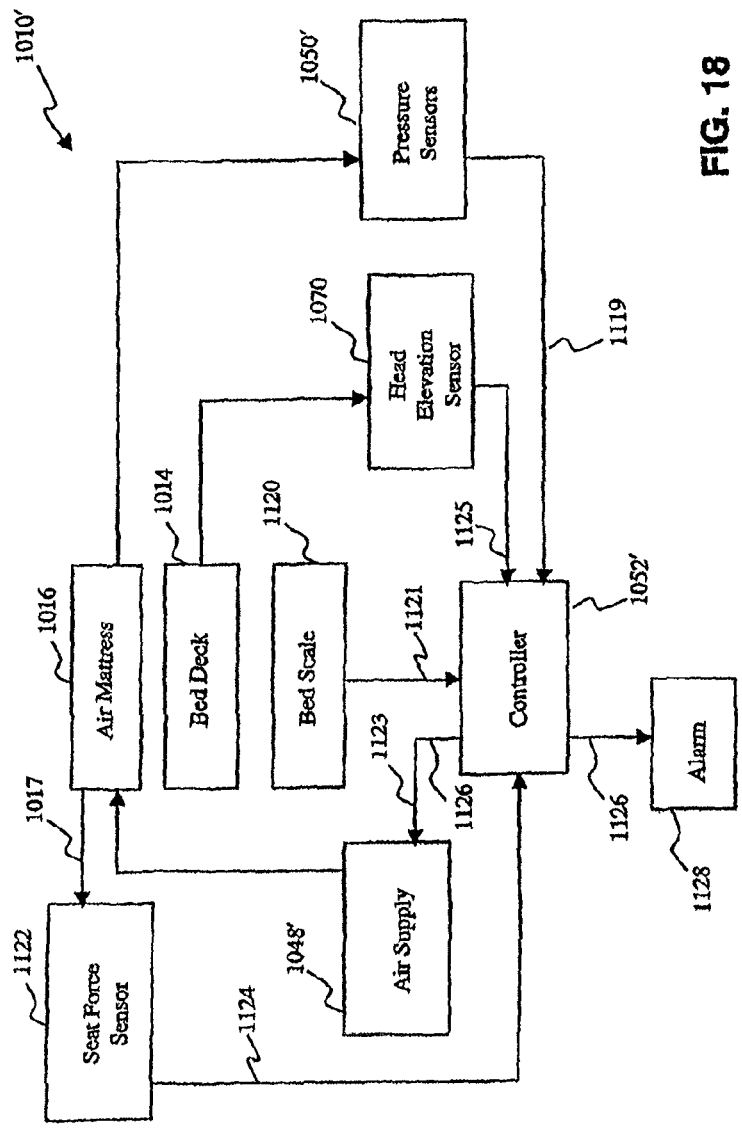
FIG. 18 is a block diagram illustrating another illustrative embodiment of the invention which includes a second force sensor in communication with the controller to provide diagnostic information verifying proper operation of a first force sensor.

In another illustrative embodiment of the present invention, diagrammatically shown in FIG. 18, a hospital bed 1010' includes a controller 1052' which automatically adjusts pressure within a patient support 16 based on a continuous feedback from a scale 1120. The scale 1120 illustratively is coupled to the frame 1012 through a plurality of load cells (not shown) and allows caregivers to weigh patients without making them leave the bed. Additional details regarding the scale 1120 are provided in U.S. Pat. No. 4,953,244 and U.S. Provisional Patent Application Ser. No. 60/365,295, which are assigned to the assignee of the present invention and are expressly incorporated herein by reference.

In the illustrated embodiment of FIG. 18, pressure sensors 1050' measure the air pressure in various zones of air mattress 1016. An output 1119 of pressure sensors 1050' and a first force output 1121 of the bed scale 1120 are input into the controller 1052'. The controller 1052' uses the signal 1121 from the bed scale 1120 to determine automatically the optimum pressure of zones 1040, 1042, and 1044 of the air mattress 1016. Controller 1052' uses the signal 1119 from pressure sensors 1050' to determine whether the pressures in air mattress 1016 need adjustment. Output 1123 from controller 1052' to an air supply 1048' keeps the air mattress 1016 at the desired pressures based on the first force output 1121 from scale 1120.

A second force sensor, illustratively a seat force sensor 1122, is coupled to the seat section 1042 of the air mattress 1016. The seat force sensor 1122 is configured to detect force transmitted to the seat section 1042 by a patient supported thereon. A second force output 1124 is transmitted by the seat force sensor 1122 to the controller 1052'. The controller 1052' uses the second force output 1124 in combination with the head elevation output 1125 from the head elevation sensor 1070 to determine a second measured weight in the manner detailed above.

The second measured weight is utilized as a diagnostic tool for verifying proper operation of the bed scale 1120. More particularly, the controller 1052' compares the first measured weight, as determined from the scale 1120, to the second measured weight, as determined from the seat force sensor 1122. If the differential between the first measured weight and the second measured weight exceeds a predetermined value, then the controller 1052' generates a diagnostic output signal 1126. The diagnostic output signal 1126 may instruct the air supply 1048' to supply fluid in order to maintain a new default baseline pressure independent of the first measured weight. Further, the diagnostic output signal 1126 may activate an alarm 1128, such as a light or an audible signal.

The foregoing description of the invention is illustrative only, and is not intended to limit the scope of the invention to the precise terms set forth. Although the invention has been described in detail with reference to certain illustrative embodiments, variations and modifications exist within the scope and spirit of the invention as described and defined in the following claims.

The invention claimed is:

1. An apparatus for supporting a patient, the apparatus comprising:
  a base;
  a frame to support the patient above the base;
  a lift coupled to the base and the frame by pivotable connections, the lift being operable to elevate a first end of the frame relative to a second end of the frame;
  a force sensor coupled to the frame, the force sensor being configured to generate a force signal in response to a detected force;
  a first angle sensor coupled to the frame, the first angle sensor being configured to generate a first angle signal representative of an angle of the force sensor, wherein the first angle sensor is spaced from the pivotable connections between the lift and the frame;
  a second angle sensor coupled to the base, the second angle sensor being configured to generate a second angle signal representative of an amount that the base is tilted;
  a controller coupled to the first and second angle sensors to receive the respective first and second angle signals therefrom and coupled to the force sensor to receive the force signal therefrom, the controller being configured to calculate a weight of the patient based on the first and second angle signals and the force signal; and an output device coupled to the controller and configured to indicate the weight of the patient.

2. The apparatus of claim 1, wherein the output device provides a visual indication of the weight of the patient.

3. The apparatus of claim 1, wherein the output device provides a printout of the weight of the patient.

4. The apparatus of claim 1, wherein the output device provides an audible indication of the weight of the patient.

5. The apparatus of claim 1, further comprising a patient support surface supported on the frame and a fluid supply configured to receive a control signal and supply a compressible medium to the patient support surface in response to the control signal.

6. The apparatus of claim 5, further comprising a pressure sensor coupled to the patient support surface to be exposed to the pressure therein, the pressure sensor being configured to generate a pressure signal in response to the pressure, wherein the controller is coupled to the pressure sensor to receive the pressure signal therefrom, and wherein the controller is configured to generate the control signal in response to the pressure signal and the weight of the patient.

7. The apparatus of claim 5, wherein the patient support surface includes a plurality of pressurizable zones, the fluid supply is further configured to distribute the compressible medium to the plurality of pressurizable zones in response to a plurality of control signals from the controller.

8. The apparatus of claim 7, wherein the pressurizable zones of the patient support surface include a head zone, a seat zone, and a foot zone.

9. The apparatus of claim 1, wherein the controller is further configured to calculate the weight of the patient based on a cosine of the angle.

10. The apparatus of claim 1, wherein the first angle sensor or the second angle sensor or both includes a dual-axis accelerometer.

11. The apparatus of claim 1, wherein the frame includes a patient support deck having a plurality of deck sections.

12. The apparatus of claim 11, wherein the plurality of deck sections includes at least one movable deck section that is movable relative to the frame.

13. The apparatus of claim 12, wherein the at least one movable deck section includes a head deck section that supports the patient's upper body.

14. The apparatus of claim 13, further comprising a head elevation sensor to measure a head angle at which the head deck section forms relative to horizontal or relative to the frame.

15. The apparatus of claim 14, wherein the controller uses the head angle in connection with calculating the weight of the patient.

16. The apparatus of claim 14, further comprising a patient support surface supported on the patient support deck and wherein the controller uses the head angle in connection with determining a target pressure for an inflatable zone of the patient support surface.

17. The apparatus of claim 1, wherein the force sensor comprises a plurality of load cells.

18. The apparatus of claim 17, wherein the force signal is based on an aggregate of load cell signals from the plurality of load cells.

19. The apparatus of claim 1, wherein the output device comprises a display carried by the frame.

20. The apparatus of claim 1, wherein the first angle sensor or the second angle sensor or both comprises a plurality of angle sensors.

21. An apparatus for supporting a patient, the apparatus comprising:
a base;
a frame to support the patient above the base,
a plurality of articulating deck sections coupled to the frame;
a lift coupled to the base and the frame by pivotable connections, the lift being operable to elevate a first end of the frame relative to a second end of the frame;
a force sensor coupled to the frame, the force sensor being configured to generate a force signal in response to a detected force;
a first angle sensor coupled to the frame, the first angle sensor being configured to generate an angle signal representative of an angle of the force sensor, wherein the first angle sensor is spaced from the pivotable connections between the lift and frame;
a second angle sensor coupled to the base, the second angle sensor being configured to generate a second angle signal representative of an amount that the base is tilted;
a controller coupled to the first and second angle sensors to receive the respective first and second angle signals therefrom and coupled to the force sensor to receive the force signal therefrom, the controller being configured to calculate a weight of the patient based on the first and second angle signals and the force signal; and
an output device coupled to the controller and configured to indicate the weight of the patient.

22. An apparatus for supporting a patient, the apparatus comprising:
a base;
a frame to support the patient above the base;
a lift coupled to the base and the frame by pivotable connections, the lift being operable to elevate a first end of the frame relative to a second end of the frame;
a plurality of force sensors coupled to the frame, each force sensor being configured to generate a force signal in response to a detected force;
a first angle sensor coupled to the frame, the first angle sensor being configured to generate a first angle signal representative of an angle of the force sensors, wherein the first angle signal comprises data indicative of an angle of movement of the frame about a transverse axis and data indicative of an angle of movement of the frame about a longitudinal axis, wherein the first angle sensor is spaced from the pivotable connections between the lift and the frame;
a second angle sensor coupled to the base, the second angle sensor being configured to generate a second angle signal representative of an amount that the base is tilted,
a controller coupled to the first and second angle sensors to receive the first and second angle signals therefrom and coupled to the force sensor to receive the force signal therefrom, the controller being configured to calculate a weight of the patient based on the first and second angle signals and the force signal; and
an output device coupled to the controller and configured to indicate the weight of the patient.

* * * * *